United States Patent [19]

Nash

[11] 4,409,820
[45] Oct. 18, 1983

[54] APPARATUS AND METHOD FOR USE IN QUANTITATIVE ANALYSIS OF A FLUID SUSPENSION

[76] Inventor: Irwin Nash, 200 Fountain St., New Haven, Conn. 06515

[21] Appl. No.: 274,482

[22] Filed: Jun. 17, 1981

[51] Int. Cl.³ .................. G01N 9/30; G01N 33/48
[52] U.S. Cl. .................................. 73/61.4; 494/10
[58] Field of Search .................. 73/61.4; 233/27, 28; 494/10

[56] References Cited

U.S. PATENT DOCUMENTS

| | | |
|---|---|---|
| 2,822,126 | 2/1958 | Cohn . |
| 3,202,348 | 8/1965 | Strohmaier ............... 73/61.4 X |
| 3,291,387 | 12/1966 | Billen . |
| 3,291,693 | 12/1966 | Brown . |
| 3,415,627 | 12/1968 | Rait . |
| 3,556,302 | 1/1971 | Agranat . |
| 3,679,367 | 7/1972 | Negersmith et al. . |
| 3,684,450 | 8/1972 | Adler et al. . |
| 3,713,775 | 1/1973 | Schmitz . |
| 3,748,101 | 7/1973 | Jones et al. . |
| 3,880,592 | 4/1975 | Kelley et al. . |
| 4,007,871 | 2/1977 | Jones et al. . |
| 4,027,660 | 6/1977 | Wardlaw et al. . |
| 4,035,156 | 7/1977 | Shumate . |
| 4,055,076 | 10/1977 | Tropea ............................ 73/61.4 |
| 4,077,396 | 3/1978 | Wardlaw et al. . |
| 4,082,085 | 4/1978 | Wardlaw et al. . |
| 4,091,659 | 5/1978 | Massey et al. . |
| 4,330,080 | 5/1982 | Mathieu ............................ 233/27 |

FOREIGN PATENT DOCUMENTS 530230 2/1977 U.S.S.R. ............................ 73/61.4

Primary Examiner—Steven L. Stephan
Assistant Examiner—Joseph W. Roskos
Attorney, Agent, or Firm—Yount & Tarolli

[57] ABSTRACT

An apparatus and method for use in the quantitative analysis of blood or a similar fluid suspension. The fluid suspension is spun about a central spin axis in a chamber which circumscribes the central spin axis and whose volume varies geometrically as it extends away from the central spin axis. A fluid sample in the chamber is allowed to separate into bands or rings circumscribing the central spin axis, with the radial extent of those rings being geometrically proportional to the volume of the components. The radial extent of those bands or rings can then be used to determine the relative amounts of the components of the fluid suspension in the chamber.

11 Claims, 7 Drawing Figures

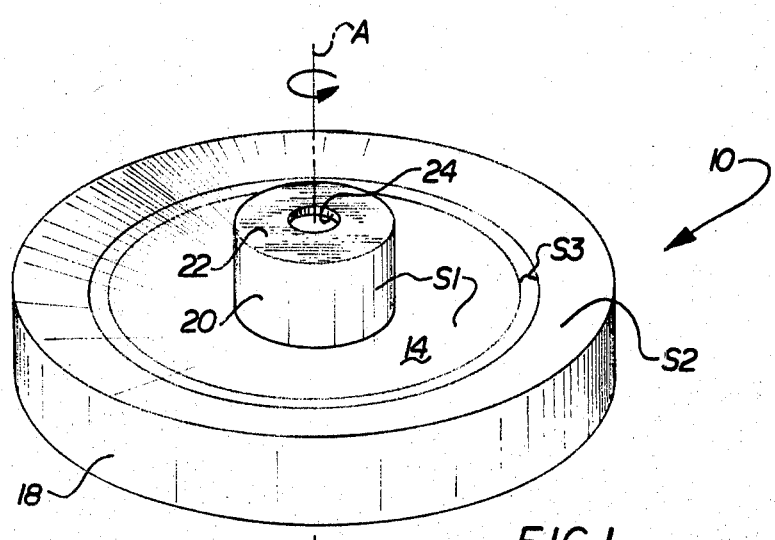
FIG. 1
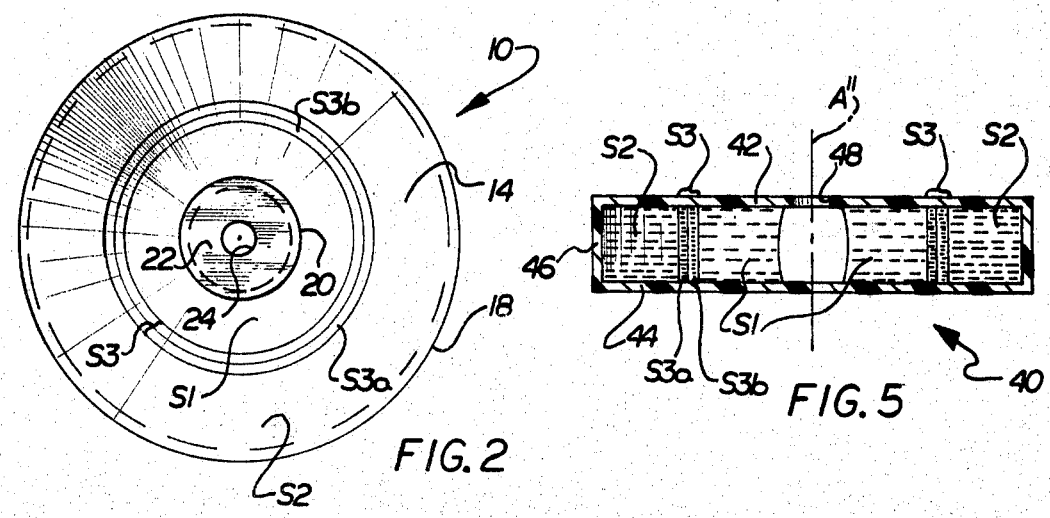
FIG. 2
FIG. 5
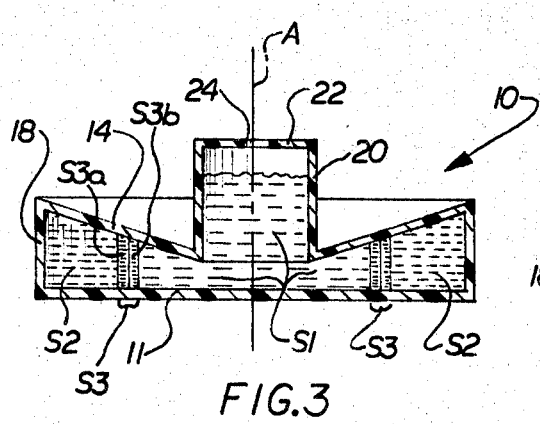
FIG. 3
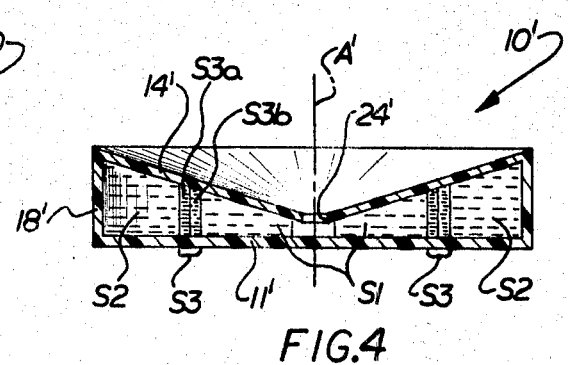
FIG. 4

APPARATUS AND METHOD FOR USE IN QUANTITATIVE ANALYSIS OF A FLUID SUSPENSION

BACKGROUND OF THE INVENTION

This invention relates to an apparatus and method for use in the quantitative analysis of a blood sample or similar type of fluid suspension.

Blood is a fluid suspension made of three basic components, plasma, red blood cells, and a buffy coat component (which includes white blood cells and platelets). The red blood cells are the most dense of the three components, and the plasma is the least dense. Further, the red blood cells and plasma comprise relatively large portions of the blood, and the buffy coat component comprises a relatively small portion of the blood.

An old and well known technique for making a quantitative analysis of a person's blood involves centrifuging a sample of blood with a device called a Wintrobe tube. Basically, a test tube is filled with a blood sample, and spun about a vertical axis. The test tube is oriented so that it extends away from the vertical axis, and as the tube is spun, centrifugal forces cause the components of the blood to seperate into layers. The tube diameter is basically constant over its length, and the length of the component layers is arithmetically proportional to their relative volume percentage of the blood sample. Thus, by measuring the length of a component layer, the relative amount of that component in the sample can be determined.

The foregoing technique has been a reasonably good one for determining the amount of red blood cells in a blood sample. However, it has not been a good technique for quantifying the white cells, because the buffy coat component occupies a very small portion of the sample, and becomes sandwiched into a narrow band between the larger volumes of red blood cells and plasma. Measurement of that narrow band is a difficult task.

Recently, a technique has been suggested for physically enlarging the axial extent of the buffy coat component in order to measure it. Specifically, U.S. Pat. No. 4,027,660 suggests insertion of a special loose plug into the centrifugal tube. The plug has a specific gravity such that it will float upon, or slightly in, the red blood cell portion. Thus, it is designed to axially spread the buffy coat component so it can be more readily measured. U.S. Pat. Nos. 4,077,396; 4,082,085; and 4,091,659 show some variations on that concept.

Other techniques for use in the analysis of a blood sample are shown in U.S. Pat. Nos. 2,822,126; 3,291,693; 3,415,627; 3,679,367; 3,684,450; 3,713,775; 3,880,592; and 4,035,156. Additionally, other types of devices for use in separating or centrifuging blood or other fluid suspensions are shown in U.S. Pat. Nos. 3,291,387; 3,556,302; 3,748,101; and 4,007,871.

SUMMARY OF THE INVENTION

This invention relates to a new and useful method and apparatus for use in the quantitative analysis of blood or a similar fluid suspension. The method and apparatus are specifically designed to quantify the buffy coat component of a blood sample.

According to the invention, a blood sample is spun about a central spin axis in a specially formed chamber circumscribing the central spin axis. The chamber includes a pair of spaced apart walls which circumscribe the central spin axis, and define a volume space that varies (preferably increases) geometrically as it extends away from the central spin axis.

As the chamer is spun about the central spin axis, the components of a blood sample in the chamber will separate into rings circumscribing the central spin axis. The red blood cells, being the most dense, will occupy the radial outermost portion of the volume space. The buffy coat (comprising of separate white cell and platelet rings) will occupy a portion of the volume space spaced closer to the central spin axis. Due to the geometry of the volume space, the buffy coat component, even though occupying a small portion of the sample, will be spread radially to a degree which then allows the buffy coat and its components to be readily measured. The relative radial extent of the red blood cells and the buffy coat can then be used to determine the relative amounts of those components of the blood sample.

A particularly useful characteristic of the apparatus of the invention is the fact that the volume space is essentially defined by the spaced apart walls of the chamber. The walls are integrally connected together to form an integral, one-piece construction with no loose parts requiring separate handling. With the apparatus and method of the invention, there is no need for a separate, specially formed plug, as found in the devices of U.S. Pat. Nos. 4,027,660; 4,077,396; 4,082,085; and 4,091,659.

Moreover, the preferred embodiment of the invention is designed in a manner which may allow quantitative analysis of the components of the buffy coat (i.e., white cells and platelets). The spaced apart walls preferably diverge from each other as they extend away from the central spin axis. The volume space occupied by the buffy coat increases geometrically, and the white blood cells and platelets may further separate into distinct annular bands whose radial extent can be measured, and used to determine the amounts of those elements.

Additionally, in the preferred embodiment, the chamber includes a fluid reservoir enveloping the central spin axis, and the spaced apart walls extend radially outward from the reservoir. The spaced apart walls define a volume space which is large enough to contain both the red blood cells and the buffy coat. The plasma occupies the reservoir, and may extend slightly into the volume space. This construction is believed to further minimize the likelihood of the plasma compressing the buffy coat.

The apparatus and method of the invention are believed to have particular utility in those circumstances where it is important to obtain a quick and reasonably accurate determination of the components of a blood sample. The apparatus and method allow simple measurement of the radial extent of the components for determining the relative amounts of the components in the blood sample.

Other characteristics and advantages of the invention will become more clearly apparent from the following description, taken with reference to the accompanying drawings wherein:

BRIEF DESCRIPTION OF THE DRAWINGS

FIG. 1 is a perspective view of an apparatus according to the invention;

FIG. 2 is a top plan view of the apparatus of FIG. 1;

FIG. 3 is a sectional view of the apparatus of FIG. 1 taken along the line 3—3 in FIG. 2;

FIG. 4 is a sectional view, similar to FIG. 3, of a further form of apparatus according to the invention;

FIG. 5 is a sectional view, similar to FIG. 3, of another form of apparatus according to the invention;

DETAILED DESCRIPTION OF THE PREFERRED EMBODIMENTS

Figure 6:
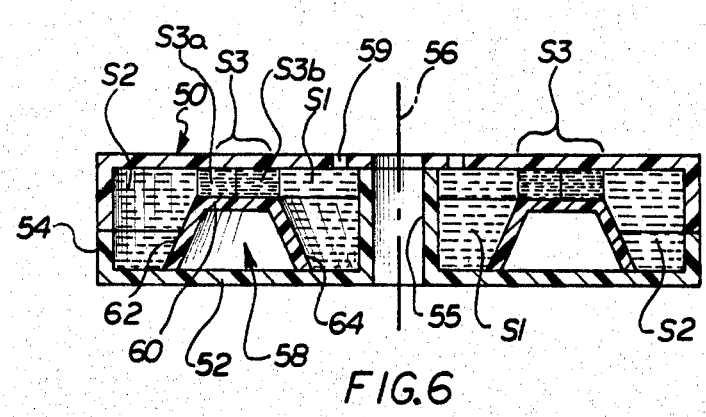
FIG. 6 is a sectional view, similar to FIG. 3, of yet another form of an apparatus constructed according to the principles of the invention.

The preferred form of the invention is shown in FIGS. 1–3. Briefly, it comprises a chamber 10 into which a blood sample is introduced, and which is spun about a vertical central spin axis A, in order to separate the blood into its component parts. The chamber 10 includes a pair of side walls 11, 14 which circumscribe the spin axis A, and an end wall 18 joining side walls 11, 14 at a location spaced from the central spin axis A. Further, it includes a reservoir formed by a cylindrical, axially extending wall 20, connected with side wall 14, and encircling or enveloping the central spin axis A.

In the apparatus of FIGS. 1–3, the side wall 11 is planar, and is oriented perpendicular to the central spin axis A. The side wall 14 is conical, and extends at an acute angle to the central spin axis A. The cylindrical wall 20, which defines the reservoir, is integrally connected with the radially inward end of the conical side wall 14. As seen from FIG. 3, the side walls 11, 14 diverge from each other as they extend away from the central spin axis A.

The space between the side walls 11 and 14 forms a volume measuring space in which the relative amounts of the red blood cell and buffy coat components are determined. As seen from FIGS. 1–3, the volume measuring space increases in circumference and width (spacing of walls 11, 14) as it extends away from the central spin axis A. Thus, the volume measuring space increases geometrically as it extends away from the central spin axis A.

When a blood sample is disposed in the chamber and the chamber spun about the central spin axis A, centrifugal forces cause the high density red blood cells to form an annular band at the radially outermost part of the volume measuring space. The plasma, the least dense component, occupies the reservoir and extends slightly into the volume measuring adjacent the reservoir. The buffy coat component, (basically comprising white blood cells and platelets) being of intermediate density, forms an annular band in the volume measuring space, between the plasma and the red blood cells.

Importantly, in the embodiment of FIGS. 1–3, the volume measuring space is large enough, in relation to the volume of the reservoir, that it can contain the entire volume of both the red blood cell component and buffy coat component of the blood sample. As the chamber 10 is spun about the central spin axis A, the fact that the volume measuring space increases geometrically as it extends away from the central spin axis A means that the relative radial portion of the volume space occupied by the component nearer the central spin axis (the buffy coat component) is fairly large and can be readily measured. The radial extent of the red blood cell band can also be readily measured. Since the geometry of the volume measuring space and the total volume of the blood sample are known, the radial extents of the red blood cell band and the buffy coat band can be used to determine the relative amounts of those components of the blood sample. Moreover, it is believed that the components of the buffy coat, i.e., white blood cells and platelets, will separate into distinct layers so that the relative amounts of those components can also be determined.

The side walls 11, 14 of the chamber 10 are translucent (preferably clear plastic). Thus, after the chamber 10 has been spun to separate the components, the relative radial extent of the bands formed by the components of the blood sample can be viewed therethrough. Preferably, after the chamber 10 has been spun, the chamber is placed against a calibrated measuring scale, to determine the relative radial extent of those bands. It is also contemplated that either of the side walls 11, 14, themselves, can be calibrated so as to facilitate visual measurement of the radial extent of the bands formed by the red blood cell and buffy coat components.

In the embodiment of FIGS. 1–3 the chamber 10 is an integral structure, comprising annular side walls 11, 14, cylindrical end wall 18 and cylindrical portion 20 forming the reservoir. Preferably, the foregoing elements of the chamber are all formed of clear plastic. The top of the cylindrical portion 20 includes a flange 22 with an opening 24 through which a blood sample is deposited into the chamber. After the blood sample is in the chamber, the opening 24 is closed by a suitable closure.

The chamber 10 can be adapted in any suitable manner to be spun about the central spin axis A. For example, the chamber can be adapted for a mating key and slot connection to a shaft which is spun about central axis A. Alternatively, the cylindrical outer wall 18 can be adopted for being engaged by apparatus which spins about axis A.

FIGS. 4 and 5 show sectional views of two other forms of a chamber according to the invention. In FIG. 4, the chamber 10' includes annular walls 11' and 14' which circumscribe the central spin axis A', and diverge from each other as they extend away from the central spin axis A'. As with the previous embodiment, the wall 11' is planar and perpendicular to the central spin axis A', and the wall 14' is conical, and diverges from central spin axis A' at an acute signal thereto. The walls 11' and 14' are connected by a cylindrical end wall 18' spaced radially from the central spin axis A'. In the embodiment of FIG. 4, there is no reservoir, and an opening 24' in the wall 14' allows a blood sample to be deposited in the chamber 10'.

In the embodiment of FIG. 5, a chamber 40 circumscribes a central spin axis A". The chamber 40 includes a pair of parallel annular spaced apart walls 42, 44. The walls 42, 44 are perpendicular to central spin axis A", and are joined together by a cylindrical end wall 46 spaced radially from the central spin axis A". The wall 42 includes an opening 48 for allowing a blood sample to be deposited in the chamber 40.

With both of the embodiments of FIGS. 4 and 5, the volume measuring space defined between the side walls increases geometrically as it extends away from the central spin axis. In the embodiment of FIG., 5, the spacing between the walls 42, 44 is constant, but the annular circumference of the volume space increases as it extends away from the central spin axis A". In the embodiment of FIG. 4, both the annular circumference of the volume space, and the width (spacing) of the walls 11, 14" increase as they extend away from the central spin axis, as in the embodiment of FIGS. 1–3.

The foregoing embodiments of the invention, described above, have several generic features. Each has a chamber with a volume measuring space at least partially formed by spaced apart side walls extending away from the central spin axis and by an end wall spaced radially from the central spin axis and joining the spaced apart side walls. Further, each form has a port or opening as a means for communicating with the fluid chamber for allowing a sample of fluid suspension to be deposited into, or removed from the chamber. In each form, the component parts of the chamber are integral, rigidly connected together, and made of suitable transparent material, such as glass, plastic, etc. One form of plastic might be medical grade polyvinylchloride.

In the forms of the invention shown in FIGS. 1-5, the chamber is a hollow disc which is annular about, and circumscribes the central spin axis. The side walls are spaced axially apart along the central spin axis and are generated by at least a portion of each of two different straight lines (one in each side wall) passing through the central spin axis, revolved about the central spin axis and moving around a closed path. The end walls are all cylindrical about the central spin axis, and the openings or ports are all on the central spin axis.

In FIGS. 1-4, the spaced apart side walls extend at acute angles relative to each other, and those side walls diverge from each other as they extend away from the central spin axis. Further, one side wall is perpendicular to the central spin axis and the other side wall is inclined relative to the central spin axis.

FIG. 5 is similar to FIG. 4, but the spaced apart side walls 42 and 44 are parallel. Further, it is contemplated that in any of the foregoing embodiments, the side walls, rather than being straight, could have a concave inward bow.

Each apparatus in FIGS. 1-5 is designed for use in the quantitive analysis of a blood sample, or similar fluid suspension. FIGS. 3-5 show in dotted lines the lines of demarcation between components of a blood sample, after the apparatus has been spun about its central spin axis. A typical blood sample S is made of three major components S1, S2 and S3, including:

(1) one larger volume component known as clear plasma, hereinafter called component S1;
(2) another larger volume component having red blood cells or RBC's (hematocrit), hereinafter called component S2; and
(3) a smaller component having a density less than component S2 and greater than component S1, comprising the buffy coat (WBC's and platelets), and hereinafter called component S3 (comprised of separate rings $S_{3a}$ white cells and $S_{3b}$ platelets).

Each apparatus will quantitate these blood components, in view of their differing behavior under centrifugal force, as its housing is spun around its central spin axis, due to the differing densities or specific gravities of the components.

As the apparatus of any of the embodiments of FIGS. 1-5 is spun about its central spin axis, centrifugal force causes the blood sample S to break down into its components S1, S2 and S3. The geometry of the fluid chamber is such that when it is spun about its central spin axis, fluid suspension sample S separates into distinct components S1, S2 and S3 (which is comprised of separate annular rings $S_{3a}+S_{3b}$ white cells and platelets, respectively) in distinct zones according to density or specific gravity. The zones comprise distinct annular rings or bands which circumscribe the central spin axis, which have radial extents geometrically proportional to the volumes of the respective component parts of the fluid suspension sample S. Thus, due to the geometric proportion of the radial extent of these annular rings to the volumes occupied by the components of fluid suspension sample S, the radial extent of the annular rings or zones can be used to determine the relative amounts of the components in the fluid suspension sample S. The relative amounts might be expressed as a percentage of the volume of the whole sample S, or as a percentage of the volume of another component.

As set forth above, in the embodiment of FIGS. 1-3, the plasma (component S1) occupies the reservoir 20 and a part of the volume measuring space between the side walls 11, 14. In the embodiments of FIGS. 4 and 5, there is no reservoir, and the entire volume between the spaced apart walls is the volume measuring space. The entire volume of fluid suspension which can be quantitated prior to introduction into the chamber will separate into the components S1, S2 and S3, and the radial extent of those components can be used to measure, and to calculate the proportions of those components of the sample. When the fluid suspension is blood, the plasma S1 is of relatively less significance than the red blood cells and the buffy cost. However, the radial extent of the plasma layer S1 may be useful in the calculation of the other layers.

Thus, in each of the foregoing examples, blood is introduced into a fluid chamber with volume measuring space large enough to contain the red blood cells and the white cell component. As the chamber is spun about a central spin axis, the blood sample will separate into its three major components. The smaller volume buffy coat component is located in the fluid chamber closer to the central spin axis than the larger volume, more dense, red blood cell component. Thus, the radial extent of the buffy coat component, compared with the radial extent of the red blood cell component, is larger per volume of component to simplify measurement of the smaller volume buffy coat component. In the embodiments of FIGS. 1-3 and 4, with diverging side walls, the buffy coat component itself may further break down into distinct zones representing its components (white blood cells and platelets), and allow quantification of those components.

The radial spread of each component in FIGS. 3-5 is increased by the geometry of the blood chamber. Component S3 thus has a substantial width so that it is better defined and more accurately measured since: (1) component S3 is closer to spin axis and has a proportionately larger radial width than component S2; (2) larger volume component S2 is radially farther from the central spin axis than component S3; (3) component S2 extends around a larger circumference; and (4) component S2 has in FIGS. 3 and 4, a greater axial extent in the volume measuring space in view of the outward taper of the side walls, or thickening of the disc toward its periphery.

Figure 7:
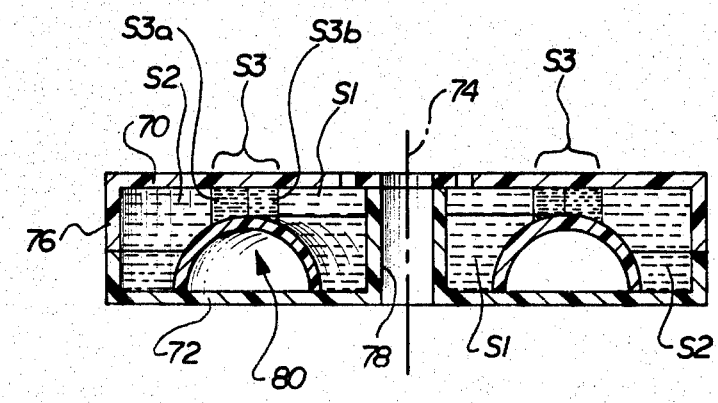
FIG. 7 is a sectional view, similar to FIG. 6, of still another form of an apparatus constructed according to the principles of the invention.

FIGS. 6 and 7 disclose still other forms of apparatus constructed according to the principles of this invention. In FIG. 6 the apparatus includes side walls 50, 52 circumscribing a central spin axis 56. Outer and inner end walls 54, 55, respectively, join the side walls 50, 52 at locations spaced from the central spin axis 56. The side walls 50 and 52 extend perpendicular to the central spin axis 56.

A central section 58 circumscribes the central spin axis 56 and extends upward from side wall 52. The central section 58 includes a wall portion 60 which is perpendicular to the central spin axis 56, and a pair of wall portions 62, 64 connected between the wall portion 60 and the side wall 52. The wall portions 62, 64 are each disposed at an angle to the central spin axis 56. With the apparatus of FIG. 6, a volume measuring space is defined partly by the central portion 58. One or more openings 59 are formed in side wall 50 and allow a blood sample to be introduced into the volume measuring space. The width of the volume measuring space (i.e., the axial spacing from the side wall 50) is reduced in the center, due to the central portion 58. However, as with the previous embodiments, the volume of the measuring space varies geometrically as it extends away from the central spin axis 56.

With the apparatus of FIG. 6, a blood sample is introduced into the volume measuring space through openings 59. The apparatus is then spun about the central spin axis 56, preferably by engagement of a shaft with the inner end wall 55. The components of the blood sample separate into annular rings whose radial extent is used to determine the relative amounts of the components of the blood sample. As the apparatus is spun, the heavier red cells can move to the the radially outermost part of the volume measuring space which has a relatively large width. The buffy coat will occupy the narrower central part of the volume measuring space, and the least dense plasma can occupy the radially innermost part of the volume measuring space which has a relatively large width. The reduced width portion 58 in the center of the measuring space increases the relative radial extent of the buffy coat component to allow its quantification. The buffy coat (and its components) can be quantified in the manner similar to that described in connection with the previous embodiments.

FIG. 7 shows an apparatus similar to FIG. 6, but with a central portion having a slightly different configuration. Specifically, in FIG. 7, a pair of side walls 70, 72 circumscribe and extend perpendicular to a central spin axis 74. A pair of end walls 76, 78 join the side walls 70, 72. A central portion 80 extends upward from side wall 72, and circumscribes central spin axis 74. The central portion 80 is curved in cross section rather than formed by straight sided wall portions as in FIG. 6. However, as with FIG. 6, the curved central portion 80 provides a reduced width in the center of the volume measuring space for spreading the buffy coat radially, and allowing quantification of the buffy coat, and its components.

It should be clear that the embodiments of FIGS. 6 and 7 work according to the principles of the previous embodiments. They provide a chamber which varies geometrically as it extends away from the central spin axis so that a fluid suspension sample in the fluid chamber separates into distinct rings circumscribing the central spin axis and having a radially extend geometrical proportional to the component parts of the fluid suspension sample. Thus, the radial extent of the rings can be used to determine the relative amounts of the component parts of the fluid suspension.

While the invention has been described in the more limited aspects of the preferred embodiment thereof, other embodiments of the invention will occur to those skilled in the art upon a reading and understanding of the foregoing specification. It is intended that all such embodiments be included within the scope of the invention as limited only by the appended claims.

I claim:

1. Apparatus for use in the quantitative analysis of a blood sample having a red blood cell component, a buffy coat and a plasma component, comprising
    an annular fluid chamber circumscribing a central spin axis,
    the annular fluid chamber including annular, axially spaced apart side walls extending away from the central spin axis and an annular end wall spaced radially from the central spin axis and joining the annular, axially spaced apart side walls,
    means communicating with the fluid chamber for allowing a sample of a blood sample to be deposited in the annular fluid chamber,
    said annular, axially spaced apart side walls and said annular end wall defining therebetween a volume measuring space which circumscribes the central spin axis and increases geometrically as it extends away from the central spin axis, the volume measuring space (i) extending radially outward to the annular end wall, (ii) including the entire space between the space apart side walls and (iii) being sufficient to completely contain at least the red blood cell and buffy coat components of the blood sample,
    the geometry of the fluid chamber guiding the red blood cell and buffy coat components of a blood sample in the fluid chamber into the volume measuring space and the geometry of the volume measuring space causing the components in the volume measuring space to separate therein into distinct concentric annular volumes of substantially fixed radial extent which extend outwardly to the annular end wall with each component within the volume measuring space filling a portion of the volume measuring space extending between the side walls and having a radial extent that is geometrically proportional to the relative amount of that component to the other components of the fluid suspension sample within the volume measuring space when said fluid chamber is spun about said central spin axis, so that measurements of the radial extent of the annular volumes in the volume measuring space can be used to determine the relative amounts of the red blood cell and buffy coat components in the volume measuring space,
    at least one of said annular, axially spaced apart side walls being translucent over the entire radial extent of the volume measuring space, thereby making the volume space translucent, and allowing the components of a blood sample in the volume measuring space to be measured therethrough.

2. Apparatus as defined in claim 1 wherein said annular fluid chamber further includes a fluid reservoir enveloping said central spin axis, said fluid reservoir being in fluid communication with said volume measuring space defined by said annular, axially spaced apart side walls.

3. Apparatus as defined in either of claims 1, or 2 wherein said annular, axially spaced apart side walls extend radially away from said fluid reservoir, said annular, axially spaced apart side walls also diverging from each other as they extend radially away from said reservoir and away from said central spin axis.

4. Apparatus as defined in claim 3 wherein one of said annular, axially spaced apart side walls comprises a planar wall disposed perpendicular to said central spin axis and the other side wall comprises a conical wall circumscribing said central spin axis, and disposed at an acute angle to said central spin axis.

5. Apparatus as defined in either of claims 1 or 2 wherein each of said annular, axially spaced apart side walls is generated by a respective straight line through the spin axis, revolved about the spin axis and moving around a closed path.

6. Apparatus as defined in either of claims 1 or 2 wherein said annular end wall is cylindrical, said means communicating with said fluid chamber comprising a port disposed on said central spin axis and in fluid communication with said fluid chamber.

7. Apparatus as defined in either of claims 1 or 2 wherein the annular, axially spaced apart side walls of said fluid chamber are parallel to each other.

8. Apparatus as defined in either of claims 1 or 2 wherein said at least one side wall that is translucent is calibrated in terms of its radial extent from said central spin axis to allow ready measurement of the relative radial extent of the components of a blood sample in said volume measuring space.

9. Apparatus as set forth in either of claims 1 or 2 wherein said volume measuring space is defined essentially by the geometry of said annular, axially spaced apart side walls and said annular end wall, and does not require the introduction of any additional means therein for spreading the buffy coat component of a blood sample into a measurable, annular volume.

10. A method of determining the relative proportions of components of a fluid suspension such as a blood sample which has a plurality of distinct components of different densities, comprising the steps of providing an annular volume measuring space between annular axially spaced side walls which extend radially away from and circumscribe a vertical spin axis and an annular end wall spaced radially from the vertical spin axis and joining the annular axially spaced side walls, and which volume measuring space extends radially outward to the annular end wall and increses geometrically as it extends radially away from the vertical spin axis, communicating a sample of the fluid suspension with the volume measuring space and spinning the volume measuring space about said vertical spin axis until the components of the fluid suspension in the volume measuring space separate into distinct concentric annular volumes of substantially fixed radial extent circumscribing the vertical spin axis and extending outward to the annular end wall of the volume measuring space, determining the radial extent of at least one distinct annular volume formed by a component of the fluid sample in the volume measuring space, and using the radial extent of that distinct annular volume formed by the component in the volume measuring space for determining the relative quantity of that component of the fluid sample in the volume measuring space.

11. A method as set forth by claim 10 wherein said fluid suspension comprises a blood sample including a red blood cell component, a buffy coat component and a plasma component, said step of spinning the annular volume measuring space comprising the step of spinning the volume measuring space until the red blood cell and buffy coat components separate into distinct, concentric annular volumes of substantially fixed radial extent in said volume measuring space, and said step of measuring the radial extent of at least one component comprises the step of measuring the radial extent of the buffy coat component.

* * * * *